United States Patent [19]

Reynolds et al.

[11] Patent Number: 4,826,326
[45] Date of Patent: May 2, 1989

[54] CRACK SIZING

[75] Inventors: William N. Reynolds, Reading; James M. Milne, Abingdon, both of United Kingdom

[73] Assignee: United Kingdom Atomic Energy Authority, London, England

[21] Appl. No.: 95,079

[22] Filed: Sep. 11, 1987

[30] Foreign Application Priority Data

Sep. 17, 1986 [GB] United Kingdom ............... 8622373
Jan. 27, 1987 [GB] United Kingdom ............... 8701703

[51] Int. Cl.$^4$ ............................................. G01N 25/72
[52] U.S. Cl. ............................................. 374/5; 374/7
[58] Field of Search ............... 374/4, 5, 112, 43, 7; 358/113

[56] References Cited

U.S. PATENT DOCUMENTS

| Re. 32,166 | 6/1986 | Berge | 374/5 X |
| 3,635,085 | 1/1972 | Shimotsuma et al. | 374/137 X |
| 3,718,757 | 2/1973 | Gulitz et al. | 374/137 X |
| 4,579,463 | 4/1986 | Rosencwaig et al. | 374/5 X |
| 4,647,220 | 3/1987 | Adams et al. | 374/5 |
| 4,671,674 | 6/1987 | Detronde | 358/113 X |

FOREIGN PATENT DOCUMENTS 0083600 10/1977 U.S.S.R. ............... 374/5

OTHER PUBLICATIONS

"Non-Destructive Examination of Fibre Composite Structure by Thermal Field Techniques", P. V. McLaughlin et al., NDT International, Apr. 1980, pp. 56–62.
"IR Non-Destructive Testing of Bonded Structures: Aspects of Theory and Practice", V. Vavilov, NDT '79 Conference, Nottingham (9/1979), [175–183, (Bulletin 7/1980)].
"Thermal and Infrared Nondestructive Testing of Composites and Ceramics", by D. R. Green, Materials Evaluation, vol. 29, No. 11, 11/1971, pp. 241–247.

Primary Examiner—Daniel M. Yasich
Attorney, Agent, or Firm—William R. Hinds

[57] ABSTRACT

A method of assessing the depth to which a crack extends below the surface of an object, or the thickness of a ligament (12) covering a crack (14), in which a thermal imager (26) is used to obtain a surface temperature profile along a line extending across the crack or ligament as heat is flowing across the surface and through the ligament. There is a steep drop in temperature across the crack or ligament, and the size of this drop at a predetermined time after the start of the heat flow may be simply related to the crack depth or ligament thickness.

14 Claims, 3 Drawing Sheets

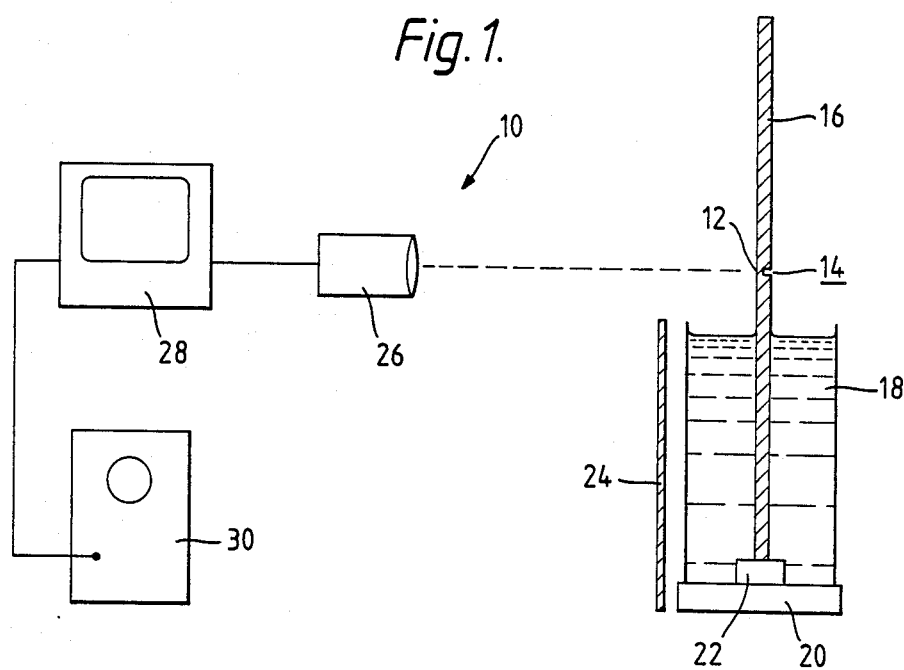
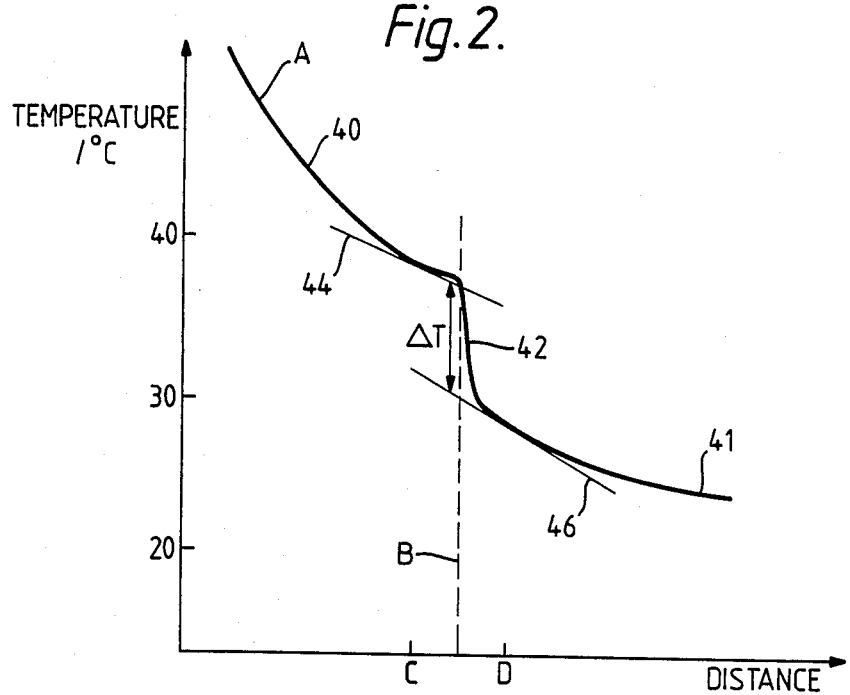

CRACK SIZING

This invention relates to a method for assessing the depth to which a crack extends below a surface of an object; and equally to a method for assessing the thickness of a ligament covering such a crack.

It is known to use ultrasonic techniques to assess the size of cracks. However such techniques are not always appropriate—for example with large grain austenitic steels crack sizing by ultrasonics is not very accurate due to signal scattering by crystal boundaries. Furthermore it is generally difficult to assess ultrasonically the depth below the surface of near-surface vertical cracks. It is also known to observe the location of defects below the surface of a plate by heating the surface and then observing the rate at which different portions of the surface cool by conduction into the bulk of the plate, one such technique being described in European Patent Application No EP 0 089 760. This technique does not however enable the depth of acrack to be assessed.

According to the present invention there is provided a method for assessing the depth to which a crack extends below a surface of an object of known thickness, or of assessing ligament thickness over a crack, the method comprising supplying heat solely to a region of the surface to one side of the crack, the region being stationary relative to the crack, so that heat flows across the surface and to the other side of the crack, and after a predetermined time measuring the temperatures of the surface at at least two points on opposite sides of the crack, and from the values of the temperatures determining the depth of the crack, or the thickness of the ligament.

In the preferred method the heat flows across the surface approximately at right angles to the crack. The heat may be supplied to the region for a short period; or it may be supplied in such a way as to maintain the heated region at a constant temperature. The surface temperatures are preferably measured by detecting the emitted radiation, typically infra-red, using a thermal scanner or a thermal imager.

In the preferred method a thermal imager is used to determine the surface temperature profile along a line approximately perpendicular to the crack orientation. The temperature gradient along the line is then measured at the location of the crack. Alternatively, two values of the temperature gradient along the line are measured at two points on opposite sides of the crack but at the same distance from the crack, and the temperature difference is then determined, at the location of the crack, between the extrapolated tangents to the profile at these two points. Both the temperature gradient at the crack, and this value of temperature difference have been found to reach steady values within a short while of the heat being supplied, and for any particular object each of these steady values is simply related to the depth of the crack, or to the thickness of the ligament.

It will be appreciated that the ligament thickness plus the crack depth equals the thickness of the object. Whether the method is measuring crack depth or ligament thickness depends principally upon whether the crack extends from the front (exposed) surface of the object or from its rear surface, but clearly the relationship between temperature values and crack depth (for a front-surface crack) and that between temperature values and ligament thickness (for a rear-surface crack) will be different. The method is applicable to cracks in welded structures as well as to those in plates though the relationship between the steady value (of temperature gradient or of temperature difference) and the crack depth or ligament thickness will differ for structures of different geometries. The relationship will also differ depending on whether heat is supplied to one side of the object (for example using infra-red lamps) or to both surfaces (for example by immersion in hot water).

The invention will now be further described, by way of example only, and with reference to the accompanying drawings in which:

FIG. 1 shows a diagrammatic view of an apparatus for assessing the thickness of a ligament covering a crack in a plate;

FIG. 2 shows a graphical representation of a temperature profile as determined by the apparatus of FIG. 1;

Figure 3:
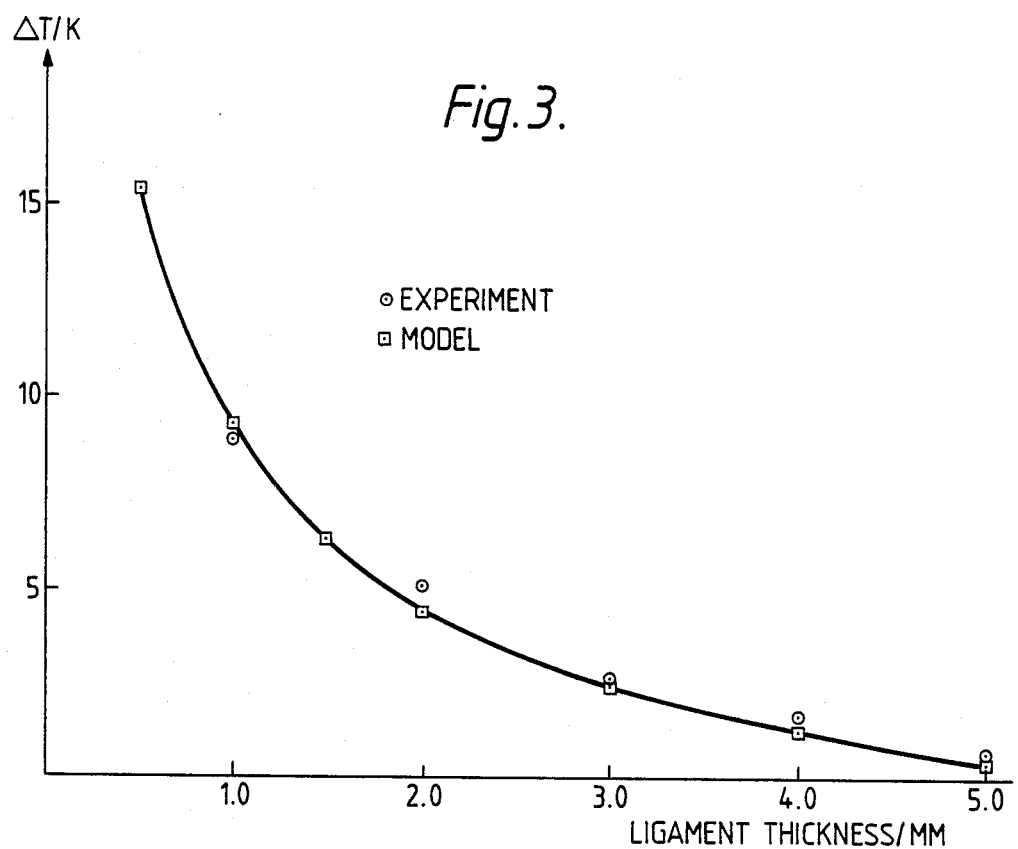
FIG. 3 shows a graphical representation of a relationship between a temperature difference and the ligament thickness.

Referring to FIG. 1 there is shown an apparatus 10 for assessing the thickness of a ligament 12 covering a horizontal crack 14 in the rear surface of a mild steel plate 16 of thickness 6.5 mm. The apparatus 10 comprises a thermostatically controlled water tank 18 heated by an electric hot-plate 20 and maintained at a constant temperature of 75° C., and a base clamp 22 to support the plate 16 upright in the tank 18. A water-cooled thermal radiation shield 24 is set up adjacent to the tank 18. The tank 18 is of such a depth that when the plate 16 is standing in it as shown, the crack 14 is 38 mm above the water-level. A video-compatible thermal imager camera 26 is arranged to view the portion of the plate 16 above and below the crack 14, the camera 26 being arranged so that the line scans are in the vertical direction. The image obtained by the camera 26 is displayed by a TV monitor 28, and individual lines of the image can be displayed on an oscilloscope 30. If desired, the images obtained by the camera 26 may be continuously recorded with a video recorder (not shown).

In operation of the apparatus 10, at time nought the plate 16, initially at room temperature, is put into the hot water tank 18. Heat flows up the plate 16 to the crack 14, and then through the ligament 12 to the part of the plate 16 above the crack 14. The camera 26 in conjunction with the monitor 28 displays an image of the temperature over the surface of the portion of the plate 16 being viewed, providing 50 frames a second each of two interleaved fields of scan lines. Individual scan lines correspond to a temperature profile along a geometrical line extending upwards along the plate surface and crossing the ligament 12; successive sets of eight scan lines corresponding to a particular geometrical line on the plate 16 are averaged and displayed on the oscilloscope 30. This averaging process reduces the noise in the temperature profile so displayed. At any particular instant the oscilloscope display, i.e. the temperature profile, can be recorded electronically or photographically.

Referring to FIG. 2, this shows a typical temperature profile (line A) crossing the ligament 12, the broken line B indicating the location of the ligament 12. The profile A consists of an approximately exponentially decreasing curve 40 in the portion of the plate below the ligament 12, a second such decreasing curve 41 in the portion above the ligament 12 and so further from the heat source, with a steep decrease 42 across the ligament 12 itself due to the increased resistance to heat flow. The thinner the ligament 12 in a particular plate 12 the greater will be the resistance to heat flow through the ligament 12, and so the larger will be the decrease 42.

A characteristic value of the size of the decrease 42 may be obtained by drawing tangents 44 and 46 to the profile at points C and D, 6 mm from the location of the ligament B in opposite directions; extrapolating the tangents 44 and 46, and measuring their separation $\Delta T$ at the location B. The value of $\Delta T$, initially zero, is found to rise with time reaching a virtually constant value after about a minute. The decrease 42 is characterised in this example by measuring the value $\Delta T$ at a time of 120 seconds after the start.

Referring to FIG. 3, this shows graphically the dependence of the measured values of $\Delta T$ upon the ligament thickness for the steel plate 16, as determined experimentally with simulated cracks 14 of known depth (i.e. slots) and as predicted by a computer model. It will be observed that the method enables the thickness of the ligament 12 of unknown thickness to be determined over a wide range of values and to an accuracy of a fraction of a millimeter.

Figure 4:
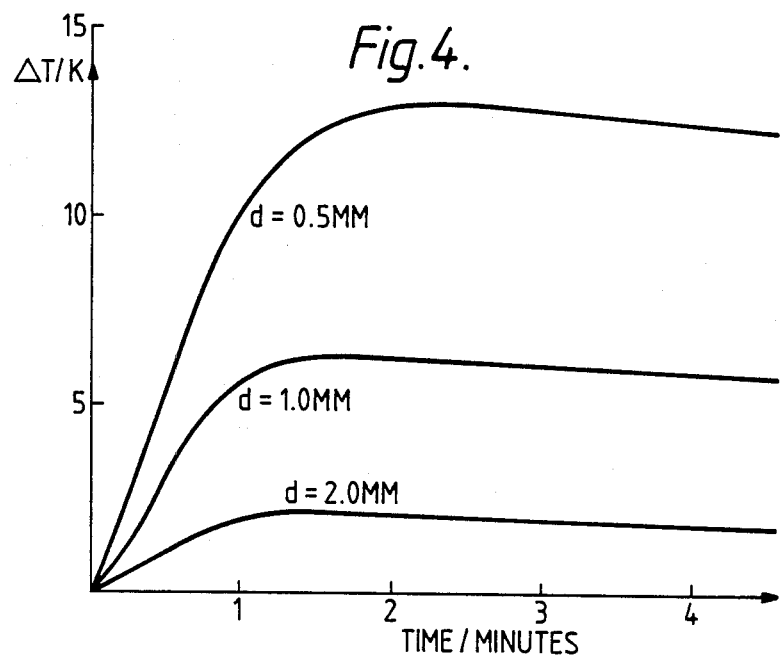
FIG. 4 shows a graphical representation of relationships between the temperature difference and time.

The virtually constant value of $\Delta T$ which is reached after a short time depends not only upon the ligament thickness but also on the thickness of the plate, the source to ligament distance, and the thermal diffusivity of the material. Referring to FIG. 4 there is shown graphically, for a number of different ligament thicknesses d, the variation of $\Delta T$ with time, as calculated from the computer model; in each case the plate is stainless steel of thickness 3.5 mm, the heat source is at 75° C., ambient temperature is 20° C., and the source to ligament distance is 20 mm. It will be observed that a maximum value of $\Delta T$ is reached after a time of between 1 and 2 minutes, and that after that time the value of $\Delta T$ is virtually constant, decreasing very slowly.

Figure 5:
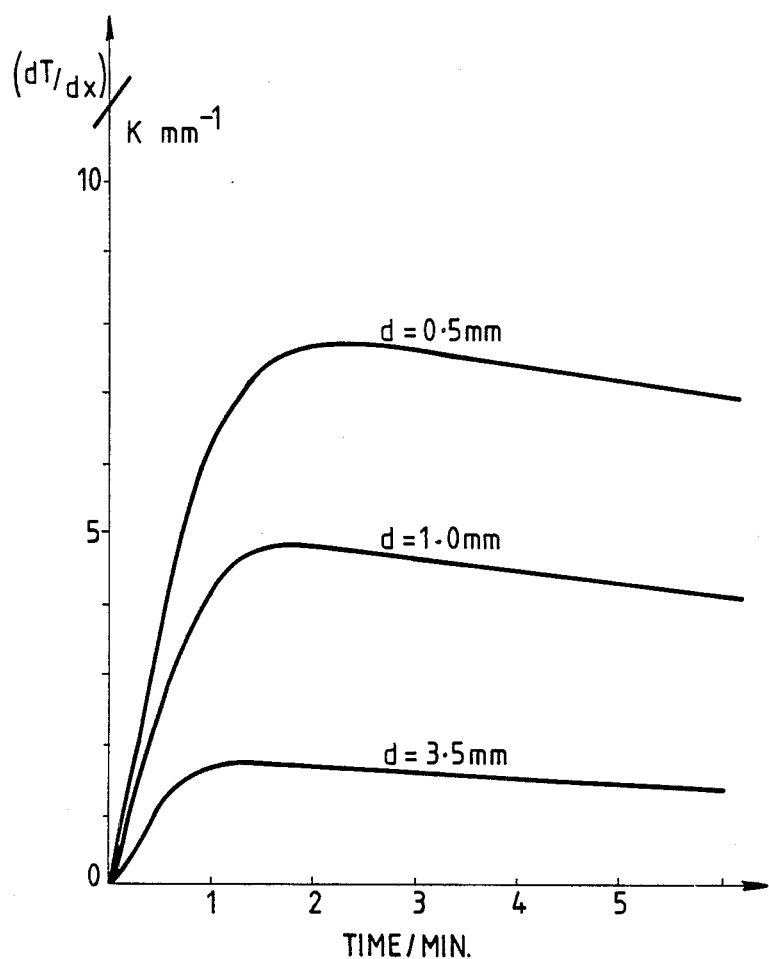
FIG. 5 shows a graphical representation of relationships between temperature gradient and time.

It will be appreciated that there are other ways in which the temperature profile obtained with the apparatus 10 can be used to assess the ligament thickness. For example the gradient of the steep decrease 42 might be measured (at its steepest point). As shown in FIG. 5, this gradient is found to rise with time, reaching a virtually constant value after about a minute in a similar manner to the variation of $\Delta T$ described above, and the value of the maximum gradient depends upon the ligament thickness in a very similar manner to the dependence of $\Delta T$ shown in FIG. 3. Thus this gradient, which may be determined from the temperature profile, may be used to assess the ligament thickness.

The graphs of FIG. 5 are as calculated by the computer model for similar situations to those of FIG. 4, i.e. a stainless steel plate of thickness 3.5 mm, a source to ligament distance of 20 mm, ambient temperature of 20° C., but a heat source at 130° C. The higher temperature heat source increases all the gradient values, but does not affect the shapes of the graphs. It will be appreciated that the graph labelled d=3.5 mm corresponds to a crack-free plate, for which there is of course a non-zero temperature gradient.

For a crack-free plate of semi-infinite extent, the temperature gradient at time t at a distance D from a source of heat at a constant temperature Tc above that of the initial plate temperature (ambient), is theoretically given by:

$$\frac{dT}{dx} = \frac{Tc}{\sqrt{(\pi at)}} \exp(-D^2/4at)$$

where a is the thermal diffusivity of the material (i.e. thermal conductivity/(density×specific heat capacity)). As is evident from FIG. 5, for a plate with a crack, the values of temperature gradient are greater the thinner the ligament. Nevertheless the time at which the maximum, substantially constant value of gradient is reached increases only slightly as the ligament thickness decreases. To ensure a steep gradient, and hence ease of measurement of the gradient, D is chosen to be a small as possible, subject to the provisos that D must be large enough to be measured accurately, and large enough that the changes do not occur too raidly to be readily observed. The time at which the gradient reaches its maximum for a defect-free plate is given by:

$$t' = D^2/2a$$

The value of D is preferably chosen such that the value of time so calculated is between about 30 and 150 seconds. The time at which the gradient of the temperature profile is measured is desirably set to be about 50% greater than the time so calculated, to ensure that the maximum, substantially constant value gradient has been achieved whatever the ligament thickness may be.

The following table provides some values of t' by way of example:

| Material | Diffusivity/ $m^2 s^{-1}$ | D = 20 mm | t'/s D = 38 mm | D = 80 mm |
|---|---|---|---|---|
| aluminium | $95 \times 10^{-6}$ | 2 | 8 | 34 |
| mild steel | $13 \times 10^{-6}$ | 15 | 56 | 246 |
| stainless steel | $4 \times 10^{-6}$ | 50 | 180 | 800 |

Thus for an aluminium object, D might be chosen to be 80 mm, and the temperature profile obtained after 50 seconds. For mild steel 38 mm is a suitable value of D, the profile being obtained after say 90 seconds. For stainless steel 20 mm is a suitable value for D, the profile being obtained after say 90 seconds.

In yet another alternative procedure a comparison might be made between the profile for a portion of the plate 16 without a crack, and for the portion with the crack 14, the two portions being at the same distance from the heat source, and the difference between the areas under the two profiles calculated in order to assess the thickness of the ligament 12.

It will also be understood that the heat source might differ from that described above. For example heat might be provided by a long straight tungsten radiant heating element (not shown) arranged parallel to the line of the crack 14 and energised to heat a strip of the plate 16 by radiation. In this case the heated strip might receive a pulse of heat rather than being held at a constant temperature as in the apparatus 10. Furthermore the method is applicable to plates of other materials than mild steel, and to objects of different shapes, such as tubes.

In each of these alternatives it will be necessary first to obtain a calibration graph either by experiment or by calculation in order to find the relationship between the temperature profile and the ligament thickness, and it will also be necessary to determine the optimum heat source/crack distance and the optimum time at which to measure the temperature profile, as discussed above.

We claim:

1. A method for assessing the depth to which a crack extends below a surface of an object of known thickness, the method comprising supplying heat solely to a region of the surface to one side of the crack, said region being stationary relative to the crack, so that heat flows across the surface and to the other side of the crack, and after a predetermined time measuring the temperatures of the surface at at least two points on opposite sides of the crack, and from the values of the temperatures determining the depth of the crack.

2. A method as claimed in claim 1 wherein the heat flows across the surface approximately at right angles to the crack.

3. A method as claimed in claim 1 wherein the surface temperatures are measured by detecting emitted radiation.

4. A method as claimed in claim 1 wherein the temperature measurements are utilised to calculate the temperature gradient along the surface along a line approximately at right angles to the crack, at the location where the line crosses the crack, from which temperature gradient the depth of the crack is determined.

5. A method as claimed in claim 1 wherein a surface temperature profile is determined along a line approximately at right angles to the crack, two values of the temperature gradient along the line are measured at two points on opposite sides of the crack but at the same distance from the crack, and the temperature difference is then determined, at the location where the line crosses the crack, between the extrapolated tangents to the profile at these two points, from which temperature difference the depth of the crack is determined.

6. A method as claimed in claim 1 wherein a surface temperature profile is determined along a line approximately at right angles to the crack; a second such profile is determined for an object identical except having no such crack, at the same time interval after supplying heat to the surface; and the difference in the areas under the two profiles calculated, from which difference the depth of the crack is determined.

7. A method as claimed in claim 1 wherein the predetermined time is between one and two times that time calculated by dividing the square of the distance between the heated region and the crack by twice the thermal diffusivity of the material of the object.

8. A method of assessing ligament thickness over a crack below the surface of an object, the method comprising supplying heat solely to a region of the surface to one side of the crack, said region being stationary relative to the crack, so that heat flows across the surface and to the other side of the crack, and after a predetermined time measuring the temperatures of the surface at at least two points on opposite sides of the crack, and from the values of the temperatures determining the thickness of the ligament.

9. A method as claimed in claim 8 wherein the heat flows across the surface approximately at right angles to the crack.

10. A method as claimed in claim 8 wherein the surface temperatures are measured by detecting emitted radiation.

11. A method as claimed in claim 8 wherein the temperature measurements are utilised to calculate the temperature gradient along the surface along a line approximately at right angles to the crack, at the location where the line crosses the crack, from which temperature gradient the thickness of the ligament is determined.

12. A method as claimed in claim 8 wherein a surface temperature profile is determined along a line approximately at right angles to the crack, two values of the temperature gradient along the line are measured at two points on opposite sides of the crack but at the same distance from the crack, and the temperature difference is then determined, at the location where the line crosses the crack, between the extrapolated tangents to the profile at these two points, from which temperature difference the thickness of the ligament is determined.

13. A method as claimed in claim 8 wherein a surface temperature profile is determined along a line approximately at right angles to the crack; a second such profile is determined for an object identical except having no such crack, at the same time interval after supplying heat to the surface; and the difference in the areas under the two profiles calculated, from which difference the thickness of the ligament is determined.

14. A method as claimed in claim 8 wherein the predetermined time is between one and two times that time calculated by dividing the square of the distance between the heated region and the crack by twice the thermal diffusivity of the material of the object.

* * * * *